United States Patent [19]
Narod et al.

[11] Patent Number: 5,912,127
[45] Date of Patent: Jun. 15, 1999

[54] METHOD AND KIT FOR EVALUATING RISK OF OVARIAN CANCER IN CARRIERS OF A BRCA1 MUTATION

[75] Inventors: Steven A. Narod, Toronto, Canada; Catherine M. Phelan, Dublin, Ireland

[73] Assignee: McGill University, Montreal, Canada

[21] Appl. No.: 08/808,195

[22] Filed: Feb. 28, 1997

Related U.S. Application Data

[60] Provisional application No. 60/012,540, Feb. 29, 1996.

[51] Int. Cl.$^6$ .............................. C12Q 1/68; C12P 19/34; C07H 21/04; C07H 21/02
[52] U.S. Cl. .............................. 435/6; 435/91.2; 435/975; 536/23.1; 536/24.31; 536/24.33; 935/77; 935/78
[58] Field of Search .............................. 435/6, 91.2, 975; 935/77, 78; 536/23.1, 24.31, 24.33

[56] References Cited

U.S. PATENT DOCUMENTS

| | | | |
|---|---|---|---|
| 5,654,155 | 8/1997 | Murphy et al. | 435/6 |
| 5,693,473 | 12/1997 | Shattuck-Eidens et al. | 435/6 |
| 5,710,001 | 1/1998 | Skolnick et al. | 435/6 |

OTHER PUBLICATIONS

Garcia–Foncillas et al. (1997) Proc. Amer. Assoc. Canc. Res. Ann. Mtg. 38:167–168. abstr.
Krontiris et al. (1993) N. Engl. J. Med. 329(8):517–523. abstr.
Aldaz et al. (1993) Canc. Res. (USA) 53(22):5339–5344. abstr.
Ford et al. (1995) Brit. J. Canc. 72(4):805–812. abstr.
Shattuck–Eidens et al., "A Collaborative Survey of 80 Mutations in the BRCA1 Breast and Ovarian Cancer Susceptibility Gene" JAMA 273: 535–541 (1995).
Struewing et al., "Detection of Eight BRCA1 Mutations in 10 Breast/Ovarian Cancer Families, Including 1 Family with Male Breast Cancer", *Am. J. Hum. Genet.* 57: 1–7 (1995).
Miki et al., "A Strong Candidate for the Breast and Ovarian Cancer Susceptibility Gene BRCA1" *Science* 226: 66–71 (1994).
Simard et al., "Common origins of BRCA1 mutation in Canadian breast and ovarian cancer families" *Nature Genetics* 8: 392–398 (1994).
Marx, J., "A Second Breast Cancer Susceptibility Gene is Found" *Science* 271: 30–31 (1996).

*Primary Examiner*—Stephanie Zitomer
*Attorney, Agent, or Firm*—Oppedahl & Larson LLP

[57] ABSTRACT

The association between the presence of one or more rare (infrequent) alleles of the HRAS variable tandem repeat (VTR) polymorphism and the incidence of ovarian cancer in women who harbor a BRCA1 mutation can be used for evaluating risk of ovarian cancer in a human patient. The patient is tested for the presence of a mutation in the BRCA1 gene; and to determine the polymorphic form of the HRAS1 variable tandem repeat region. The presence of both a mutation in the BRCA1 gene and a rare polymorphic form of the HRAS1 variable tandem repeat region is indicative of an elevated risk of developing ovarian cancer. A kit for performing this evaluation includes reagents necessary for performing a test for the BRCA1 mutation and to evaluate the polymorphic form of the HRAS1 variable tandem repeat region.

4 Claims, 1 Drawing Sheet

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
          (A) ORGANISM: human (xi) SEQUENCE DESCRIPTION: SEQ ID NO:1:

GAGCTAGCAG GGCATGCCGC                                                  20

(2) INFORMATION FOR SEQ ID NO:2:

(i) SEQUENCE CHARACTERISTICS:
          (A) LENGTH: 20
          (B) TYPE: nucleic acid
          (C) STRANDEDNESS: single
          (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
          (A) ORGANISM: human (xi) SEQUENCE DESCRIPTION: SEQ ID NO:2:

AGCACGGTGT GGAAGGAGCC                                                  20
```

(2) INFORMATION FOR SEQ ID NO:3:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (xi) SEQUENCE DESCRIPTION: SEQ ID NO:3:

TTCTCTCCAG GGGACGCCA                                                                               19

METHOD AND KIT FOR EVALUATING RISK OF OVARIAN CANCER IN CARRIERS OF A BRCA1 MUTATION

This application is a regular application claiming priority from U.S. Provisional Patent Application No. 60/012,540 filed Feb. 29, 1996.

BACKGROUND OF THE INVENTION

This application relates to a method and kit for evaluating the risk of ovarian cancer in an individual carrier of a BRCA1 mutation.

It is generally accepted that early detection of cancer enhances the likelihood of successful treatment. Because of this, considerable research has focused on identifying genetic causes of cancer which would permit identification of an at-risk individual prior to the actual onset of cancer. Recently, the BRCA1 gene has been identified and isolated, and it has been shown that there is a substantial relationship between mutations in this gene and breast and ovarian cancer. Specifically, women who carry a mutation in the BRCA1 gene have an 80% risk of breast cancer and a 40% risk of ovarian cancer to age 70. Easton, et al., "Breast and ovarian cancer incidence in BRCA1- mutation carriers," *Am J Hum Genet* 56: 265–271 (1995).

While testing for BRCA1 mutations offers a method of identifying at-risk individuals, it is apparent from these percentage risks that many woman who harbour a BRCA1 mutation will not develop cancer. Thus, simply testing for BRCA1 mutations could lead to prolonged monitoring of women who are not going to develop cancer, or even to inappropriate prophylactic intervention. It would therefore be desirable to have methods for evaluating individuals who harbour a BRCA1 mutations to further refine that individual's risk of actually developing breast or ovarian cancer.

It is an object of the present invention to provide such a method for refining an individual carrier of a BRCA1 mutation's risk of developing ovarian cancer.

It is a further object of the present invention to provide a kit for use in testing for risk of developing ovarian cancer.

SUMMARY OF THE INVENTION

We have now determined that there is an association between the presence of one or more rare (infrequent) alleles of the HRAS variable tandem repeat (VTR) polymorphism and the incidence of ovarian cancer in women who harbor a BRCA1 mutation, Thus, one aspect of the present invention is a method for evaluating risk of ovarian cancer in a human patient, comprising the steps of (a) testing the patient for the presence of a mutation in the BRCA1 gene; and (b) testing the patient to determine the polymorphic form of the HRAS1 variable tandem repeat region, wherein the presence of both a mutation in the BRCA1 gene and a rare polymorphic form of the HRAS1 variable tandem repeat region is indicative of an elevated risk of developing ovarian cancer. A further aspect of the invention is a kit for performing this evaluation comprising reagents necessary for performing a test for the BRCA1 mutation and to evaluate the polymorphic form of the HRAS1variable tandem repeat region.

DETAILED DESCRIPTION OF THE INVENTION

Figure 1:
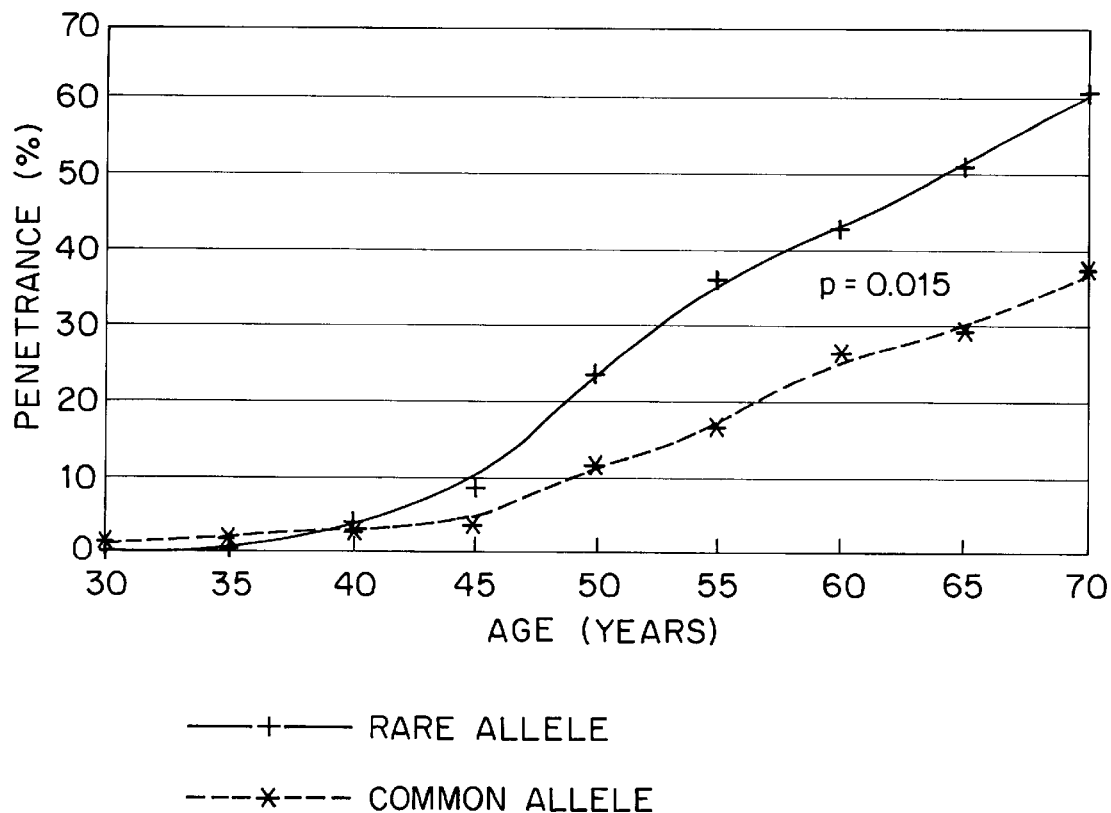
FIG. 1 shows the age-specific penetrances of ovarian cancer for women with and without rare alleles of HRAS1.

To investigate if the HRAS minisatellite modifies the penetrance of the BRCA1 gene, we have determined allele sizes for 307 female BRCA1 carriers from 80 different breast cancer and breast-ovarian cancer families. BRCA1 carriers were identified by a combination of linkage analysis and direct gene sequencing. We estimate that more than 98% of these women carry BRCA1 mutations, and for 266 women (86.6%) the mutation has been identified. Following PCR amplification and Southern blotting, individual alleles were visualized by hybridization of an oligonucleotide specific to the HRAS1 repeat unit. The allele sizes and frequencies of the 307 cases are given in Table 1. The five most common alleles have VTR sizes of 0.97, 1.09, 1.45, 1.59, and 2.50 kilobases, and occur at frequencies of 56%, 7.2%, 7.0%, 8.8%, and 5.2%, respectively. All other alleles occur at frequencies of less than 2% and are considered to be rare.

TABLE 1

| VTR Allele Size (kilobases) | all 307 women | 173 Breast Cancer | 42 Ovarian Cancer | 112 Unaffected |
|---|---|---|---|---|
| .90 | 5 | 2 | 2 | 1 |
| .94 | 6 | 2 |  | 4 |
| 0.97 | 346 | 202 | 42 | 122 |
| 0.99 | 13 | 7 | 5 | 4 |
| 1.05 | 10 | 6 | 2 | 3 |
| 1.07 | 6 | 5 | 3 |  |
| 1.09 | 44 | 20 | 4 | 22 |
| 1.14 | 2 | 2 | 1 |  |
| 1.25 | 3 | 2 |  | 1 |
| 1.35 | 2 | 2 | 1 |  |
| 1.40 | 7 | 3 |  | 4 |
| 1.45 | 66 | 37 | 8 | 29 |
| 1.55 | 3 |  | 2 | 1 |
| 1.65 | 2 | 1 |  | 1 |
| 1.75 | 1 | 1 |  |  |
| 1.90 | 3 | 1 | 1 | 2 |
| 2.0 | 54 | 28 | 6 | 19 |
| 2.08 | 1 |  |  | 1 |
| 2.15 | 1 |  |  | 1 |
| 2.38 | 2 | 2 |  |  |
| 2.44 | 1 |  |  | 1 |
| 2.50 | 32 | 22 | 6 | 6 |
| 2.55 | 3 | 1 |  | 2 |
| 2.60 | 1 |  | 1 |  |

Subjects with a history of ovarian cancer were found to carry a rare allele more frequently (40.4%) than subjects without ovarian cancer (19.2%, relative risk 2.85; p=0.002). There was no association between the presence of a rare allele and a history of breast cancer; only 36 of the 137 cases (20.8%) of breast cancer were carriers of rare alleles (RR= 0.84; p=0.52). Thus, identifying the presence of a rare allele of VTR size is a good prognostic indicator of risk of ovarian cancer in women who also have a BRCA1 mutation.

Thus, in order to evaluate risk of ovarian cancer in a human patient, it is advantageous to perform two steps (a) testing the patient for the presence of a mutation in the BRCA1 gene; and (b) testing the patient for the presence of an abnormal polymorphic form of the HRAS1 variable tandem repeat region. These two steps can be performed concurrently or sequentially. The presence of both a mutation in the BRCA1 gene and an abnormal polymorphic form of the HRAS1 variable tandem repeat region is indicative of an elevated risk of developing ovarian cancer.

Testing of a patient for the presence of a mutation in the BRCA1 gene can be performed using any of a number of known methods which have been employed to date, including sequencing of the BRCA1 gene, single-stranded conformational polymorphism, hybridization with allele-specific oligonucleotide probes or heteroduplex analysis. See International Patent Nos. WO96/05306, WO96/05307, and WO96/05308, which are incorporated herein by reference, Friedman, et al. "Confirmation of BRCA1 by analysis of germline mutations linked to breast and ovarian cancer in ten families," *Nature Genetics* 8: 399–404 (1994); Hogervorst, et al., "Rapid detection of BRCA1 mutations by the protein truncation test," *Nature Genetics* 10: 208–212 (1995); Serova et al., *Amer. J. Human Gen.* 58: 42–51 (1996). In addition, where certain BRCA1 mutations are found to be more prevalent in a population, it may be advantageous to tailor the test to for BRCA1 mutations to focus on the more prevalent mutation or mutations when used for testing of such a population. Thus, for example, we have found that one BRCA1 mutation in exon 2 of the BRCA1 gene, 185delAG, is a common mutation in Jewish women of Ashkenazi heritage. Testing of patients of Ashkenazi heritage might therefore focus initially on this mutation.

Testing to determine the VTR size can be carried out using restriction fragment length polymorphism as described in Krontiris et al., "An association between the risk of cancer and mutations in the HRAS1 minisatellite locus," *New Engl J Med* 329: 517–523 (1993); Green, et al., "Allelic variation of reporter gene activation by the HRAS1 minisatellite locus," *New Engl J Med* 329: 517–523 (1993) or Decorte et al., "Rapid detection of hypervariable regions by the polymerase chain reaction technique," *DNA and Cell Biology* 9: 461–469 (1990), or using PCR to amplify the VTR region followed by an analysis of the amplicon lengths. Analysis of amplicon lengths can be performed by Southern Blotting as described in the example below, but could also be performed using gel electrophoresis. In this case, it is advantageous to include a label, for example a radio-label or a fluorescent label such a fluorescein, on the amplification primer to render the amplicons directly detectable within the electrophoresis gel.

Reagents for practicing the two steps of the method of the invention can be packaged together to form a kit in accordance with the invention. Such a kit comprises, in packaged combination, (a) reagents for testing the patient for the presence of a mutation in the BRCA1 gene; and (b) reagents for testing the patient for the presence of a rare form of the HRAS1 variable tandem repeat region.

Suitable reagents for use in testing for a mutation in the BRCA1 gene include sequencing primers specific to one or more exons of the BRCA1 gene, allele-specific probes specific to one or more known mutations of the BRCA1 gene, and/or amplification primers specific for amplification of one or more exons of the BRCA1 gene. Suitable reagents for testing the patient for the presence of a rare form of the HRAS1 variable tandem repeat region include amplification primers which amplify the VTR region.

EXAMPLE

Women were included in the study if they were likely to be carriers of a mutant BRCA1 gene, regardless of whether or not they had been diagnosed with cancer. A total of 307 female carriers were identified among 80 families. For 55 of these families (55) the BRCA1 mutation has been identified. Women were determined to be carriers by direct sequencing, or by a combination of direct sequencing and linkage analysis. Because not all BRCA1 mutations are detectable by sequencing the coding region of the gene, breast and breast-ovary families were also included if there was an 80% or greater chance that they were linked to BRCA1. Probabilities of BRCA1 linkage were established by combining clinical data with the lod score generated by chromosome 17 q markers. The likelihood of a family with three or more breast or ovarian cancers being linked to BRCA1 increases with the number of ovarian cancers; these probabilities are estimated to be 92% for two or more ovarian cancers, 81% for a single ovarian cancer case and 45% for site-specific breast cancer families. Overall, the mean likelihood of being a BRCA1 mutation carrier was estimated to be 98.9% for the 307 women in the study. Of these, 153 women had been diagnosed with breast cancer, 32 women have had ovarian cancer, 20 women with both breast and ovarian cancer, and 112 women were currently unaffected, or had died of another cause.

Determination of HRAS Allele Size: We investigated the incidence of the rare alleles of HRAS in the 307 BRCA1 carriers using the following PCR assay. 0.25 ug of genomic DNA from the lymphoblastoid cell line or from fresh blood were amplified in a 25 ul reaction using 1 uM of the following primers:

HRAS-1; 5'GAGCTAGCAGGGCATGCCGC3' SEQ ID No.: 1 and

HRAS-2; 5'AGCACGGTGTGGAAGGAGCC3'. SEQ ID No.: 2

The reaction also contained 2 mM MgCl2, 10 mM β-mercaptoethanol, 1.7 ug/ml BSA, 10% DMSO and 0.5 mM of each dNTP. The PCR cycle included one cycle of 94° C. for 10 minutes, then 25 cycles of 94° C. for one minute, 68° C. for three minutes and 72° C. for seven minutes. This was followed by an extension cycle of 10 minutes at 72° C.

The PCR amplified products were analyzed by Southern Blotting and Hybridisation. All 25 ul of the samples were run on a 2% agarose gel or a 3% composite gel consisting of 2% agarose: 1% Nusieve (FMC, ME, USA) at 100V for 16 hours. The gel was then denatured in 0.4M NaOH for 30 minutes and the DNA was then transferred to a nylon membrane overnight using a dry blotting method. The following day the membrane was neutralized and the DNA was fixed to the membrane by UV-crosslinking (Stratalinker, Stratagene). An oligonucleotide was designed from the consensus sequence in the repeat as follows:

5' TTCTCTCCAGGGGACGCCA3'. SEQ ID No.: 3

The oligo was end-labeled for one hour at 37° C. using T4 polynucleotide kinase (New England Biolabs) and $^{32}$P-dATP (Amersham) and hybridised at 42° C. overnight to the membrane in a solution containing 6×SSC, 10×Denhardts soln, 5% Dextran sulphate, 1% SDS and 100 ug/ml of salmon sperm DNA and human placental DNA. The membranes were washed in the following solutions and times: 1) 2×SSC, 0.1% SDS - 10 minutes., 2) 1×SSC, 0.1% SDS - 10 minutes 3) 0.5×SSC, 0.1% SDS 10 minutes, and then exposed to Kodak X-omat R film for approximately 10 hours.

The original studies of the HRAS VTR were done by sizing the alleles on Southern blots after restriction enzyme digestion. To ensure that both methods were equivalent, we performed both the RFLP method and the PCR method on 20 individuals. It was possible to detect all of the large alleles by using the PCR method and the interpretation of the polymorphisms was equivalent. The PCR technique permits the resolution of alleles in the 2.45 to 2.60 kb range that differ by as little as one repeat unit.

Statistical analysis: The association between a rare HRAS allele and the presence of breast or ovarian cancer in BRCA1 carriers was first assessed by a comparing the proportions of affected and unaffected women who carried one or more rare HRAS1 alleles. Statistical significance was measured with the Chi-squared test. To adjust for the variable lengths of follow-up in these women, a Cox proportional hazards model was employed. Under this model a historical cohort of 307 carriers was constructed and followed from age 20 until either the development of breast or ovarian cancer, prophylactic breast or ovarian surgery, death from another cause, or January 1995. The presence or absence of rare HRAS-1 allele was then entered as a covariate in the proportional hazards model.

The average age of the women in this study was 48.7 years. In order to account for age differences in study subjects (range 20 to 95 years), and to adjust for different periods of risk, the data set was analysed using a Cox proportional hazards model. Women were considered to be at risk for ovarian cancer until their current age or, if deceased, until the age of death. Women who underwent a prophylactic oophorectomy were removed from the risk group at the age at which surgery was performed. The relative risk for ovarian cancer in the proportional hazards model was 2.11 (p=0.012). The risk of ovarian cancer in this cohort was estimated to be 43.1% to age 70. Although this study was not designed to measure the cumulative incidence of cancer among BRCA1 carriers, this figure is very close to earlier estimates. The age-specific penetrances of ovarian cancer for women with and without rare alleles are presented in FIG. 1.

The penetrance of breast cancer in this cohort was 83.2% to age 70. Survival analyses revealed no modification of breast cancer penetrance by the presence of a rare HRAS allele, or by the relative position of the mutation in the BRCA1 gene.

To assess the possibility that the HRAS effect on ovarian cancer risk was primarily due to allele size, as opposed to allele frequency, we analysed the data after grouping subjects into those with large and small alleles. There were no significant differences in ovarian cancer risk between the three groups of women with 0, 1, or 2 small alleles.

We claim:

1. A method for evaluating risk of ovarian cancer in a human patient, comprising the steps of
   (a) testing the patient for the presence of a mutation in the BRCA1 gene; and
   (b) testing the patient for the presence of an rare polymorphic form of the HRAS1 variable tandem repeat region, wherein the presence of both a mutation in the BRCA1 gene and an rare polymorphic form of the HRAS1 variable tandem repeat region is indicative of an elevated risk of developing ovarian cancer.

2. The method of claim 1, wherein the HRAS1 variable tandem repeat region is tested by amplifying the variable tandem repeat region to form an amplification product and determining the size of the amplification product.

3. A kit for evaluating risk of ovarian cancer in a human patient, comprising in packaged combination
   (a) one or more reagents for testing the patient for the presence of a mutation in the BRCA1 gene; and
   (b) one or more reagents for testing the patient for the presence of a rare polymorphic form of the HRAS1 variable tandem repeat region.

4. The kit of claim 3, wherein the reagents for testing the patient for the presence of a rare polymorphic form of the HRAS1 variable tandem repeat region includes a pair of amplification primers for polymerase chain reaction amplification of the variable tandem repeat region.

* * * * *